US00PP29367P3

(12) United States Plant Patent
Finn

(10) Patent No.: US PP29,367 P3
(45) Date of Patent: Jun. 12, 2018

(54) BLACKBERRY PLANT NAMED 'COLUMBIA SUNRISE'

(50) Latin Name: ***Rubus subg. Rubus* Watson.**
Varietal Denomination: Columbia Sunrise

(71) Applicant: The United States of America, as represented by the Secretary of Agriculture, Washington, DC (US)

(72) Inventor: Chad E Finn, Corvallis, OR (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days. days.

(21) Appl. No.: 15/330,508

(22) Filed: Sep. 29, 2016

(65) Prior Publication Data

US 2018/0092267 P1 Mar. 29, 2018

(51) Int. Cl.
*A01H 5/08* (2018.01)

(52) U.S. Cl.
USPC ..... Plt./203
CPC ..... *A01H 5/0887* (2013.01)

(58) Field of Classification Search
USPC ..... Plt./203
See application file for complete search history.

*Primary Examiner* — Susan McCormick Ewoldt
(74) *Attorney, Agent, or Firm* — John Fado; Ariel Atkinson

(57) ABSTRACT

A new and distinct blackberry cultivar that originated from seed produced from a cross between the female blackberry plant 'NZ 9629-1' (unpatented) and the male parent blackberry plant 'ORUS 1939-2' (unpatented). This new blackberry cultivar can be distinguished by its medium to high yields of medium-large and very sweet flavored berries with good firmness and color and that are the earliest ripening, completely thornless blackberry that we are aware of.

4 Drawing Sheets

Latin name of the genus and species of the plant claimed: 'COLUMBIA SUNRISE' is a blackberry plant that is *Rubus* subg. *Rubus* Watson.

Variety denomination: The new blackberry plant claimed is of the variety denominated 'Columbia Sunrise' *Rubus* subg. *Rubus* Watson.

BACKGROUND OF THE INVENTION

The present invention relates to a new and distinct blackberry cultivar designated 'Columbia Sunrise' and botanically known as *Rubus* subg. *Rubus* Watson. This new blackberry cultivar was discovered in Corvallis, Oreg. in July 2008 and originated from a cross between the female blackberry plant 'NZ 9629-1' (unpatented) and the male parent blackberry plant 'ORUS 1939-2' (unpatented). 'Columbia Sunrise's spinelessness is derived from 'Lincoln Logan' (unpatented) that can be found as a parent four and five generations back in 'Columbia Sunrise's pedigree. The original seedling of the new cultivar was asexually propagated at a nursery in Benton County, Oreg. The new cultivar was established in vitro from a cane cutting, and microcuttings have been taken and rooted from this sort of culture. The present invention has been found to be stable and to reproduce true to type through successive asexual propagations.

BRIEF DESCRIPTION OF THE PHOTOGRAPHS

This new blackberry plant is illustrated by the accompanying photographs that show the fruit of the plant and machine harvested fruit, as well as canes and entire plants; the colors shown are as true as can be reasonably obtained by conventional photographic procedures.

DETAILED DESCRIPTION OF THE NEW CULTIVAR

Figure 1:
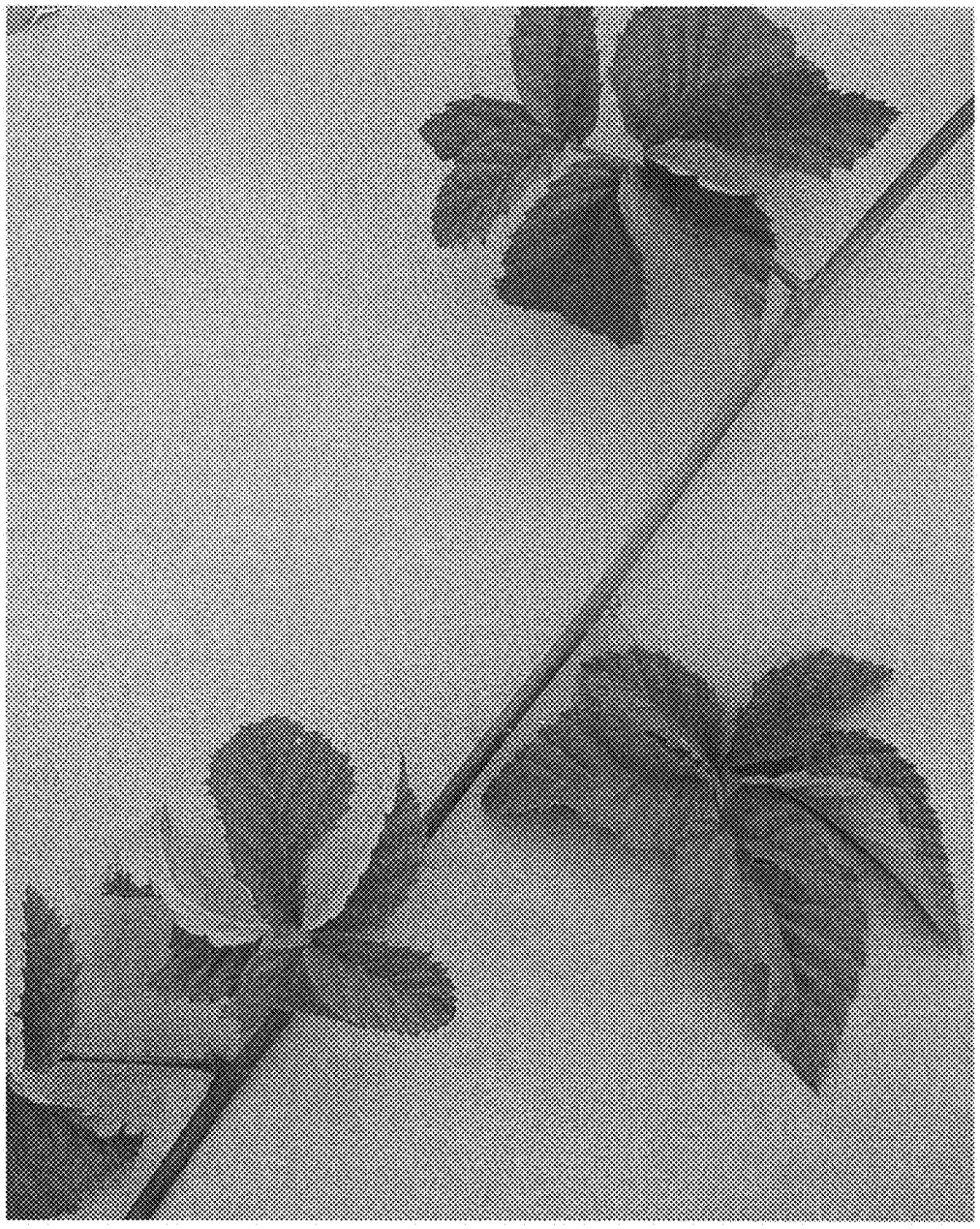
FIG. 1 shows a section of a spineless primocane and a leaf.
Figure 2:
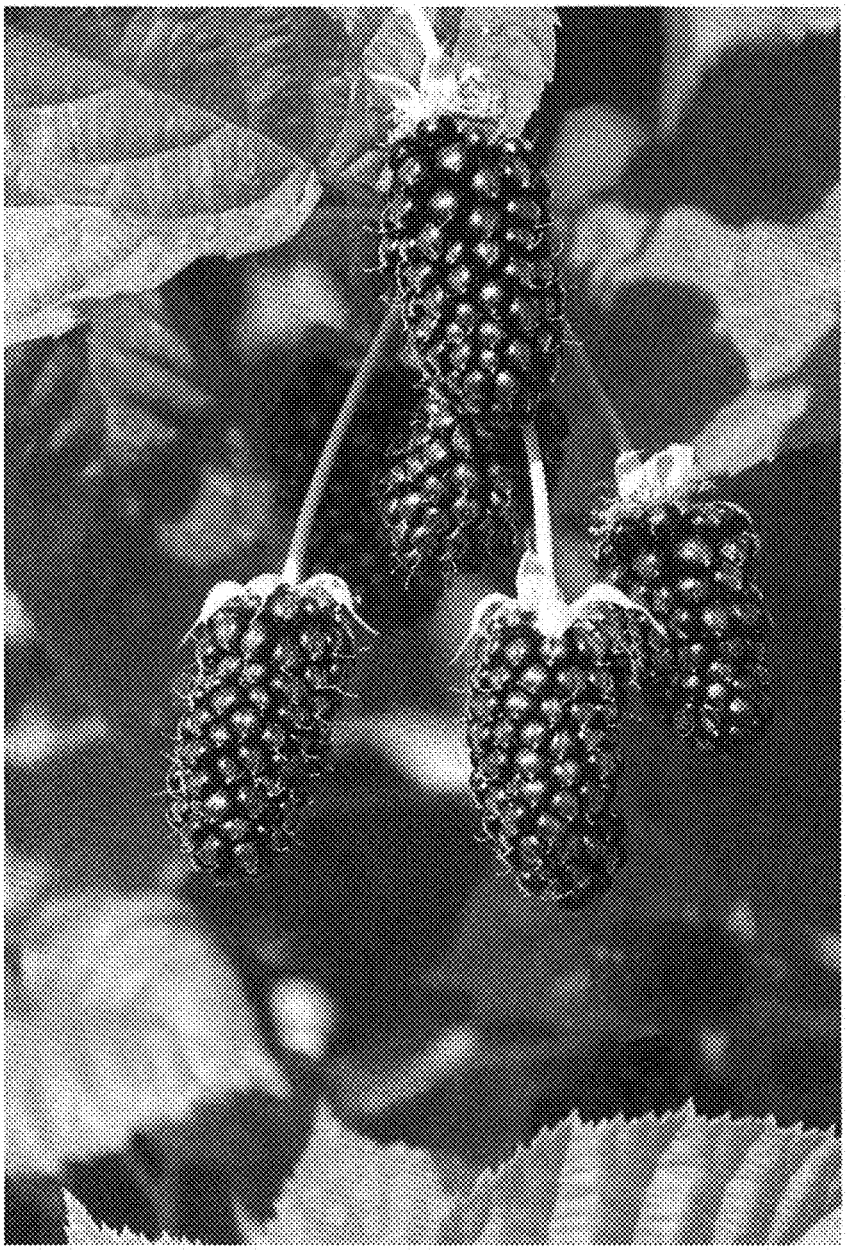
FIG. 2 shows typical fruit in a fruit cluster in the field.
Figure 3:
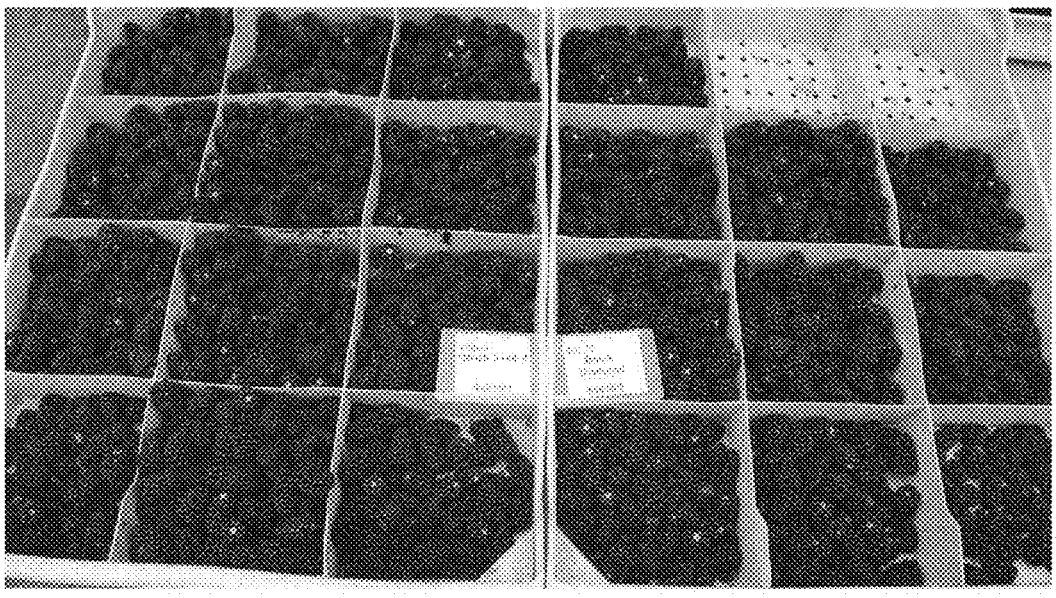
FIG. 3 shows typical hand-harvested fruit of 'Columbia Sunrise' (left) compared to 'Black Diamond' (unpatented) (right).
Figure 4:
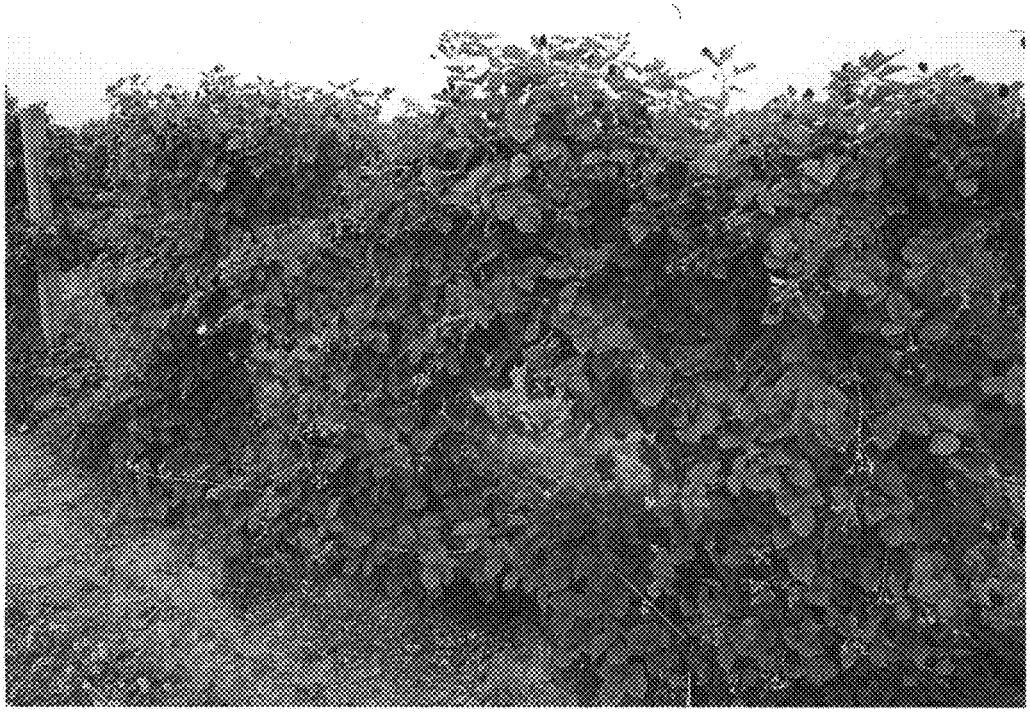
FIG. 4 shows an entire 4-year old plant.

The following description of 'Columbia Sunrise' is based on observations taken from 2011 to 2016 growing seasons in trials in Corvallis and Aurora, Oreg. This description is in accordance with UPOV terminology. Color designations, color descriptions and other phenotypical descriptions may deviate from the stated values and descriptions depending upon variation in environmental, seasonal, climatic and cultural conditions. 'Columbia Sunrise' has not been observed under all possible environmental conditions. Color terminology follows The Royal Horticultural Society Colour Chart. London (R.H.S.) ($5^{th}$ edition, 2007).

Table 1 shows plant characteristics of the new cultivar. Characteristics include plant vigor, growth habit, date of full bloom, date 50% of fruit were ripe, weight of primary fruit, and winter tolerance in Aurora, Oreg. (45° 16' 49" N/122° 44' 50" W) and Lynden, Wash. (48° 56' 48" N/122° 27' 2" W).

TABLE 1

Plant Characteristics of 'Columbia Sunrise'.

| Characteristic | Columbia Sunrise |
|---|---|
| Plant vigor | High compared to Black Diamond |
| Growth habit | Trailing |
| Date full bloom | 5 May, early compared to Marion |
| Date 50% of fruit were ripe | 5 July, early compared to Black Diamond |
| Weight of primary fruit | 8.15 g (larger than Marion) |
| Winter tolerance in Aurora, Oregon (45° 16' 49" N/122° 44' 50" W) | Good-very good |
| Winter tolerance in Lynden, Washington (48° 56' 48" N/122° 27' 2" W) | Good (similar to Marion) |

Table 2 shows floricane and mature primocane characteristics of the new cultivar. Characteristics include diameter at base, diameter at midpoint, diameter at terminus, internode length at base, internode length at midpoint, internode length at terminus, presence of spines further than 0.6 m from the soil surface, presence of spines less than 0.6 m from the soil surface, floricane color at base, floricane color at midpoint, floricane color at terminus, floricane lateral length, floricane lateral strength, primocane color at base, primocane color at midpoint, primocane color at terminus, floricane length, and floricane length (range).

TABLE 2

Floricane and Mature Primocane Characteristics of 'Columbia Sunrise'.

| Characteristic | Columbia Sunrise |
|---|---|
| Diameter at base | 1.27 cm |
| Diameter at midpoint | 0.89 cm |
| Diameter at terminus | 0.39 cm |
| Internode length at base | 4.60 cm |
| Internode length at midpoint | 7.27 cm |
| Internode length at terminus | 8.25 cm |
| Presence of spines further than 0.6 m from the soil surface | Absent |
| Presence of spines less than 0.6 m from the soil surface | Absent |
| Floricane color at base | 200A |
| Floricane color at midpoint | 146C |
| Floricane color at terminus | 144B |
| Floricane lateral length | Medium-long |
| Floricane lateral strength | Medium |
| Primocane color at base | 144B with tint 178A |
| Primocane color at midpoint | 146C |
| Primocane color at terminus | 146C |
| Floricane length | 3.26 m |
| Floricane length (range) | 1.51-4.59 m |

Table 3 shows primocane foliage characteristics of the new cultivar. Primocane characteristics include mature compound leaf width, mature compound leaf length, number of leaflets per primocane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, spine presence on leaves, pubescence on primocane leaflet upper surface, pubescence on primocane leaflet undersurface, primocane leaf color abaxial, primocane leaf color adaxial, petiole length, petiole color: upper surface, petiole color: undersurface, petiolule length terminal leaflet, petiolule length first distal leaflet, petiolule color abaxial, petiolule color adaxial, stipule length, stipule width, and stipule attitude.

TABLE 3

Primocane Foliage Characteristics of 'Columbia Sunrise'.

| Characteristic | Columbia Sunrise |
|---|---|
| Mature compound leaf width | 17.78 cm |
| Mature compound leaf length | 13.87 cm |
| Number of leaflets per primocane compound leaf | 7.00 |
| Mature leaflet shape | Cordate |
| Mature leaflet apex | Broadly acuminate |
| Mature leaflet base | Rounded to cordate; distal often oblique |
| Mature terminal leaflet width | 6.34 cm |
| Mature terminal leaflet length | 8.03 cm |
| Mature first lateral leaflet width | 3.23 cm |
| Mature first lateral leaflet length | 5.38 cm |
| Leaflet margin | Double serrate |
| Leaflet serration teeth length | 0.22 cm |
| Leaflet serration teeth width at base | 0.26 cm |
| Spine presence on leaves | No |
| Pubescence on primocane leaflet: upper surface | Light pubescent. Hairs short and soft |
| Pubescence on primocane leaflet: undersurface | Puberulent-dense mat |
| Primocane leaf color abaxial | 146A |
| Primocane leaf color adaxial | 147B |
| Petiole length | 8.15 cm |
| Petiole color: upper surface | 166A |
| Petiole color: undersurface | 145A |
| Petiolule length: terminal leaflet | 1.14 cm |
| Petiolule length: first distal leaflet | Sessile |
| Petiolule color: abaxial | 149B |
| Petiolule color: adaxial | 149B |
| Stipule length | 1.26 cm |
| Stipule width | 0.18 cm |
| Stipule attitude | Erect, sometimes recurved, often crossed |

Table 4 shows floricane foliage characteristics of the new cultivar. Floricane characteristics include mature compound leaf width, mature compound leaf length, number of leaflets per floricane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, pubescence on floricane leaflet: upper surface, pubescence on floricane leaflet undersurface, floricane leaf color abaxial, floricane leaf color adaxial, petiole length, petiole color adaxial, petiole color abaxial, petiolule length terminal leaflet, petiolule length first distal leaflet, petiolule color abaxial, petiolule color adaxial, stipule length, and stipule width.

TABLE 4

Floricane Foliage Characteristics of 'Columbia Sunrise'.

| Characteristic | Columbia Sunrise |
|---|---|
| Mature compound leaf width | 12.98 cm |
| Mature compound leaf length | 11.62 cm |
| Number of leaflets per floricane compound leaf | 3, sometimes 4 |
| Mature leaflet shape | Cordate |
| Mature leaflet apex | Broadly acute to broadly acuminate |
| Mature leaflet base | Cordate |

TABLE 4-continued

Floricane Foliage Characteristics of 'Columbia Sunrise'.

| Characteristic | Columbia Sunrise |
|---|---|
| Mature terminal leaflet width | 6.40 cm |
| Mature terminal leaflet length | 7.78 cm |
| Mature first lateral leaflet width | 5.00 cm |
| Mature first lateral leaflet length | 6.93 cm |
| Leaflet margin | Serrate |
| Leaflet serration teeth length | 0.35 cm |
| Leaflet serration teeth width at base | 0.32 cm |
| Pubescence on floricane leaflet: upper surface | Yes; light |
| Pubescence on floricane leaflet: undersurface | Yes; light |
| Floricane leaf color abaxial | 137B |
| Floricane leaf color adaxial | 147B |
| Petiole length | 5.92 cm |
| Petiole color adaxial | 146B |
| Petiole color abaxial | 146B |
| Petiolule length terminal leaflet | 1.45 cm |
| Petiolule length first distal leaflet | 1.58 cm |
| Petiolule color: abaxial | 145A |
| Petiolule color: adaxial | 145A |
| Stipule length | 0.95 cm |
| Stipule width | 0.13 cm |

Table 5 shows flower and flowering characteristics of the new cultivar. Flower and flowering characteristics include date 1$^{st}$ bloom, date full bloom, date last bloom, petal color, number flowers per cluster, number of petals per flower, flower diameter, petal length, petal width, number of sepals per flower, peduncle length, rachis length, peduncle color, and cyme type.

TABLE 5

Flower and Flowering Characteristics of 'Columbia Sunrise'.

| Characteristic | Columbia Sunrise |
|---|---|
| Date 1$^{st}$ bloom | 28-Apr |
| Date full bloom | 5-May |
| Date last bloom | 19-May |
| Petal color | 155C |
| Number flowers per cluster | 4.67 |
| Number of petals per flower | 5.00 |
| Flower diameter | 3.40 cm |
| Petal length | 1.47 cm |
| Petal width | 1.09 cm |
| Number of sepals per flower | 5.33 |
| Peduncle length | 21.50 cm |
| Rachis length | 15.02 cm |
| Peduncle color | 146C |
| Cyme type | Elongate simple cyme |

Table 6 shows fruit and fruiting characteristics of the new cultivar. Fruit and fruiting characteristics include date 5% of fruit were ripe, date 50% of fruit were ripe, date 95% of fruit were ripe, weight of primary fruit, weight of secondary fruit, weight of tertiary fruit, diameter of primary fruit at equator, diameter of 2° fruit at equator, diameter of 3° fruit at equator, diameter of 1° fruit at poles: tip, diameter of 1° fruit at poles: base, diameter of 2° fruit at poles: tip, diameter of 2° fruit at poles: base, diameter of 3° fruit at poles: tip, diameter of 3° fruit at poles: base, berry length primary fruit, berry length 2° fruit, berry length 3° fruit, ratio of primary fruit length to width, shape description, uniformity of berry shape, color when full ripe, number of drupelets per fruit, drupelet weight, individual seed weight, glossiness, firmness, flavor, texture of fruit when chewed, drupelet skin resistance to abrasion, ease of separation of fruit from pedicel, machine harvestability, resistance to heat damage of fruit, berries per inflorescence—mean, berries per inflorescence range, soluble solids (%; in brix), pH, titratable acidity (% as citric acid), and yield (actual kg·plt$^{-1}$).

TABLE 6

Fruit and Fruiting Characteristics of 'Columbia Sunrise'.

| Characteristic | Columbia Sunrise |
|---|---|
| Date 5% of fruit were ripe | 25 June |
| Date 50% of fruit were ripe | 5 July |
| Date 95% of fruit were ripe | 19 July |
| Weight of primary fruit | 8.15 g |
| Weight of secondary fruit | 7.77 g |
| Weight of tertiary fruit | 8.38 g |
| Diameter of primary fruit at equator | 2.00 cm |
| Diameter of 2° fruit at equator | 1.88 cm |
| Diameter of 3° fruit at equator | 1.92 cm |
| Diameter of 1° fruit at poles: tip | 1.25 cm |
| Diameter of 1° fruit at poles: base | 1.64 cm |
| Diameter of 2° fruit at poles: tip | 1.46 cm |
| Diameter of 2° fruit at poles: base | 1.81 cm |
| Diameter of 3° fruit at poles: tip | 1.00 cm |
| Diameter of 3° fruit at poles: base | 1.79 cm |
| Berry length primary fruit | 3.50 cm |
| Berry length 2° fruit | 3.31 cm |
| Berry length 3° fruit | 3.76 cm |
| Ratio of primary fruit length to width | 1.75 |
| Shape description | Conical |
| Uniformity of berry shape | Excellent |
| Color when full ripe | 202A |
| Number of drupelets per fruit | 104.83 |
| Total seed weight per fruit | 200.57 mg |
| Individual seed weight | 1.93 mg |
| Glossiness | Medium glossy to dull |
| Firmness | Moderate |
| Flavor | Excellent |
| Texture of fruit when chewed | Excellent |
| Drupelet skin resistance to abrasion | Good |
| Ease of separation of fruit from pedicel | Easy |
| Machine harvestability | Excellent |
| Resistance to heat damage of fruit | Good |
| Berries per inflorescence-mean | 6.50 |
| Berries per inflorescence range | 5-8 |
| Soluble solids (%; in Brix) | 13.00 |
| pH | 3.40 |
| Titratable acidity (% as citric acid) | 18.30 |
| Yield (actual kg · p1t$^{-1}$) | 4.7 |

COMPARISON WITH PARENTAL AND COMMERCIAL VARIETIES

'Columbia Sunrise' differs from the female parent 'NZ 9629-1' (unpatented) in that 'Columbia Sunrise' has medium-sized, glossy, fruit (8.2 g), while 'NZ 9629-1' has slightly pubescent fruit that are smaller (4.5 g).

'Columbia Sunrise' differs from the male parent blackberry plant 'ORUS 1939-2' (unpatented) in that it is spineless, has conic and sweet berries and moderate to high yields, while 'ORUS 1939-2' (unpatented) is spiny and has barrel shaped berries that tend to have a higher incidence of purple vs black fruit and moderate yields.

'Columbia Sunrise' differs from the commercial variety 'Marion' (unpatented) in that 'Columbia Sunrise' is spineless, very early ripening and has medium-large (8.2 g), firm fruit while 'Marion' is spiny and ripens the crop in midseason and has medium yields of medium sized (5.0 g), and soft fruit that are unevenly shaped. 'Columbia Sunrise' differs from the commercial variety 'Black Diamond' (unpatented) in that 'Columbia Sunrise' carries the 'Lincoln Logan'

(unpatented) source of spinelessness and therefore the canes are completely spineless and the plants are vigorous with medium-large (8.2 g) fruit that are an excellent, sweet, aromatic flavor, while 'Black Diamond' (unpatented) carries the 'Austin Thornless' (unpatented) source of spinelessness and so has spines on the base of the canes and the plants are not vigorous and they produce smaller (5.2 g) fruit with a mild flavor. 'Columbia Sunrise' differs from the commercial variety 'Columbia Star' (U.S. Plant Pat. No. 25,532) based predominantly on having less uniformly shaped and sweeter fruit that ripen 7 days earlier.

We claim:

1. A new and distinct cultivar of blackberry plant, substantially as illustrated and described, characterized by its medium to high yields of medium-large and very sweet flavored berries with good firmness and color and that are the earliest ripening, completely thornless cultivar that we are aware of.

* * * * *